United States Patent
Breton et al.

(10) Patent No.: US 6,562,353 B1
(45) Date of Patent: *May 13, 2003

(54) DESQUAMATION/EPIDERMAL RENEWAL OF THE SKIN AND/OR COMBATING SKIN AGING

(75) Inventors: Lionel Breton, Versailles (FR); Christel Liviero, Paris (FR)

(73) Assignee: Societe L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/305,213

(22) Filed: May 5, 1999

(30) Foreign Application Priority Data

May 12, 1998 (FR) .............................. 98 05967

(51) Int. Cl.⁷ .............................. A61K 7/00; A61K 7/42; A61K 31/19
(52) U.S. Cl. ........................... 424/401; 424/59; 514/557
(58) Field of Search .............................. 424/401, 78.02, 424/78.03, 59; 514/938, 887, 557

(56) References Cited

U.S. PATENT DOCUMENTS

| 4,595,586 | A | * | 6/1986 | Flom .......................... 424/59 |
| 4,791,217 | A | * | 12/1988 | Robert et al. |
| 5,093,109 | A | * | 3/1992 | Mausner |
| 5,536,500 | A | * | 7/1996 | Galey et al. |
| 5,610,185 | A | * | 3/1997 | Stanwell et al. ............. 514/544 |
| 5,652,228 | A | * | 7/1997 | Bissett ........................ 514/77 |
| 5,874,463 | A | * | 2/1999 | Ancira |
| 5,876,736 | A | * | 3/1999 | Cohen et al. ................ 424/401 |
| 5,932,232 | A | * | 8/1999 | De Salvert et al. ......... 424/401 |
| 6,054,137 | A | * | 4/2000 | Breton et al. ................ 424/400 |
| 6,264,962 | B1 | * | 7/2001 | Breton et al. ................ 424/401 |
| 6,267,971 | B1 | * | 7/2001 | Breton et al. ................ 424/401 |

FOREIGN PATENT DOCUMENTS

GB          2304573 A    *    3/1997

OTHER PUBLICATIONS

RD 400038 A, Aug. 1997, RD, anonymous.*

* cited by examiner

Primary Examiner—Jose' G. Dees
Assistant Examiner—Marina Lamm
(74) Attorney, Agent, or Firm—Burns, Doane, Swecker & Mathis, L.L.P.

(57) ABSTRACT

Cinnamic acid and derivatives thereof are well suited for promoting desquamation and/or stimulating epidermal renewal and/or combating intrinsic/extrinsic aging of the skin of a human subject in need of such treatment, by topically applying thereto, for such period of time as required to elicit the desired response, a cosmetically/therapeutically effective amount of cinnamic acid and/or of at least one derivative thereof.

13 Claims, No Drawings

DESQUAMATION/EPIDERMAL RENEWAL OF THE SKIN AND/OR COMBATING SKIN AGING

CROSS-REFERENCE TO PRIORITY APPLICATION

This application claims priority under 35 U.S.C. §119 of FR-98/05967, filed May 12, 1998, hereby expressly incorporated by reference.

BACKGROUND OF THE INVENTION

1. Technical Field of the Invention

The present invention relates to promoting desquamation of the skin and/or stimulating epidermal renewal and/or combating aging of the skin by topical application thereto of cinnamic acid or derivative thereof, or composition comprising same.

The compounds/compositions of this invention are especially well suited for promoting desquamation of the skin and/or stimulating epidermal renewal and/or combating intrinsic and/or extrinsic aging of the skin, as well as for nontherapeutically treating the skin to promote desquamation and/or combat aging of the skin.

2. Description of the Prior Art

Desquamation is a natural phenomenon associated with the fact that the epidermis, which constitutes the upper layer of the skin, is in constant regeneration. The epidermis consists of several layers of cells, the deepest of which is the basal layer consisting of undifferentiated cells. These cells differentiate and migrate towards the surface of the epidermis over time, constituting the various layers thereof, until they form at the surface of the epidermis the corneocytes, which are dead cells, which are removed by desquamation. This loss of surface is compensated for by the migration of cells from the basal layer towards the surface of the epidermis. This entails perpetual renewal of the skin. Forced removal of the horny layer accelerates the renewal and makes it possible to combat aging.

At the same time, these cells continue their differentiation, the final stage of which is the corneocyte. These are dead cells which make up the final layer of the epidermis, namely, the outermost layer also known as the *Stratum corneum*.

Aging of the skin resulting from the effects of intrinsic or extrinsic factors on the skin is reflected by the appearance of wrinkles and fine lines, by yellowing of the skin which develops a parchment-like appearance accompanied by the appearance of pigmentation blemishes, by the disorganization of the elastin and collagen fibers, causing a loss of elasticity, flexibility and firmness, and by the appearance of telangiectases.

Certain of these signs of aging are more particularly associated with intrinsic or physiological aging, namely, with "normal" aging due to age or chronobiological aging, whereas others are more specific to extrinsic aging, namely, aging caused in general by the environment; this relates more particularly to photoaging due to exposure to sunlight, to light or to any other radiation, whether natural or artificial.

The present invention relates to not only intrinsic or physiological aging, but also to extrinsic aging.

The changes in the skin due to intrinsic aging are the consequence of a genetically programmed senescence involving endogenous factors. This intrinsic aging causes, in particular, a slowing down or retarding of the renewal of the skin cells, which is reflected essentially by the appearance of clinical impairments such as reduction in the subcutaneous adipose tissue and the appearance of small wrinkles or fine lines, and by histopathological changes such as an increase in the number and thickness of elastic fibers, a loss of vertical fibers from the membrane of the elastic tissue, and the presence of large irregular fibroblasts in the cells of this elastic tissue.

By contrast, extrinsic aging causes clinical impairments such as large wrinkles and the formation of a flaccid and weathered skin, and histopathological changes such as excessive accumulation of elastic material in the epidermis and degeneration of the collagen fibers.

Various active agents suggested for combating aging of the skin are known in the prior art.

Thus, U.S. Pat. No. 4,603,146 describes the use of retinoic acid and derivatives thereof in cosmetic compositions for combating skin aging.

Moreover, many patents and publications (see, for example, EP-A-413,528) describe, and numerous commercially available commercial cosmetic compositions include, α-hydroxy acids, such as lactic acid, glycolic acid or citric acid, for treating aging of the skin.

Too, the β-hydroxy acids, and more especially salicylic acid and derivatives thereof, are known for their desquamating properties (see WO-A-93/10756 and U.S. Pat. No. 4,767,750).

All of the aforesaid prior art compounds elicit action against aging of the skin by promoting desquamation, i.e., the removal of the "dead" cells located at the surface of the horny layer of the epidermis. This "desquamating" property is also referred to, often incorrectly, as a keratolytic property.

However, the compounds of the prior art also present objectionable side effects, such as stinging, tautness and sensations of overheating and redness which are unpleasant for the user.

Need therefore continues to exist for antiaging agents having an action which is at least as effective as that of the compounds of the prior art, but which do not present the disadvantages thereof.

SUMMARY OF THE INVENTION

Accordingly, a major object of the present invention is the provision of active agents for promoting desquamation of the skin and/or for stimulating epidermal renewal, while at the same time avoiding the stinging, tautness or sensations of overheating or redness which are unpleasant for the user and which to date have characterized the state of this art.

Briefly, it has now surprisingly and unexpectedly been determined that topically applying an effective amount of cinnamic acid or of at least one derivative thereof onto the skin promotes the desquamation thereof and/or stimulates epidermal renewal and therefore combats skin aging.

Thus, this invention features formulating an effective amount of cinnamic acid or at least one derivative thereof into cosmetic/therapeutic compositions that promote desquamation of the skin and/or stimulate epidermal renewal and/or combat intrinsic and/or extrinsic aging of the skin.

The present invention also features a non-therapeutic regime/regimen for treating the skin to promote desquamation thereof and/or to stimulate epidermal renewal and/or to combat intrinsic and/or extrinsic aging of the skin.

DETAILED DESCRIPTION OF BEST MODE AND SPECIFIC/PREFERRED EMBODIMENTS OF THE INVENTION

More particularly according to the present invention, it will be appreciated that cinnamic acid is present in transform in the essential oils of basil and of cinnamon, in Peruvian balsamine and in cacao leaves. The cis-form is present in the oil from *Alpinia malacensis*.

In the prior art, cinnamic acid or derivatives thereof have been formulated into compositions for preventing bedsores (JP-07,242,558), as anti-ultraviolet active agents (U.S. Pat. No. 5,093,109), in permanent-waving compositions (DE-3, 301,515, DE-2,912,477 and EP-22,996), in hair lotions (JP-7,053,401 and JP-3,041,413), in depigmenting compositions (JP-5,221,845 and JP-1,186,811) and as antioxidants (EP-664,290).

However, to date the use of cinnamic acid or derivative thereof for promoting desquamation of the skin and/or stimulating epidermal renewal and/or combating intrinsic and/or extrinsic aging of the skin was unknown.

The present invention therefore features the use of an effective amount of cinnamic acid or of at least one derivative thereof, or composition comprised thereof, to promote desquamation of the skin and/or to stimulate epidermal renewal and/or to combat intrinsic and/or extrinsic aging of the skin.

The cinnamic acid or derivative thereof can be of natural or synthetic origin. By the term "natural origin" is intended cinnamic acid or derivative thereof prepared from plant material in which they exist in the natural state. By the term "synthetic origin" is intended cinnamic acid or derivative thereof, prepared via chemical synthesis or biotechnology.

Thus, the term "cinnamic acid" connotes cinnamic acid or derivative thereof, of natural or synthetic origin, in purified form, or in any preparation comprising same.

Exemplary cinnamic acid derivatives according to the invention, include, for example, mono- and polyhydroxycinnamic acids, alcohols, aldehydes, esters and derivatives thereof.

Cinnamic acid is the preferred compound according to the invention.

Too, the cinnamic acid or derivative thereof can be used either alone or in any admixture of same.

The amount of cinnamic acid or derivative thereof which can be used according to the invention obviously depends on the desired effect and should be an amount which is effective for promoting desquamation of the skin and/or stimulating epidermal renewal and/or combating intrinsic and/or extrinsic aging of the skin.

For example, the amount of cinnamic acid or of at least one derivative thereof according to the invention advantageously ranges, for example, from $10^{-6}\%$ to 10% and preferably from $10^{-3}\%$ to 5% of the total weight of the composition.

This invention also features compositions for promoting desquamation of the skin and/or stimulating epidermal renewal and/or combating intrinsic and/or extrinsic aging of the skin, comprising an effective amount of at least cinnamic acid or at least one derivative thereof, formulated into appropriate cosmetically/dermatologically acceptable medium therefor (diluent, vehicle or carrier).

In the compositions of the invention, the cinnamic acid or at least one derivative thereof can be present in an amount ranging from $10^{-6}\%$ to 10% and preferably from $10^{-3}\%$ to 5% of the total weight of the composition.

This invention also features a nontherapeutic regime/regimen for promoting desquamation of the skin and/or stimulating epidermal renewal and/or combating intrinsic and/or extrinsic aging of the skin, comprising topically applying a cosmetic composition containing an effective amount of cinnamic acid or derivative thereof onto the skin.

The subject compositions can be formulated into any known pharmaceutical form such as, for example, as an emulsion, in particular an oil-in-water or water-in-oil emulsion, or even in the form of a multiple emulsion.

They may also be provided in the form of an aqueous solution, which may be gelled, or in the form of a lotion, for example.a two-phase lotion, an ointment, a cream, a milk or a mousse (foam).

The compositions according to this invention may comprise an oily phase based on animal, plant, mineral, silicone, fluoro and/or synthetic oil.

The oily phase may also comprise fatty alcohols or fatty acids, as well as surfactants.

Exemplary are the hydrocarbon-based oils such as liquid paraffin or liquid petroleum jelly; perhydrosqualene; arara oil, sweet almond oil, beauty-leaf oil, palm oil, castor oil, avocado oil, jojoba oil, olive oil or cereal germ oil; alcohols such as oleyl alcohol, linoleyl alcohol, linolenyl alcohol, isostearyl alcohol or octyldodecanol. Also exemplary are the silicone oils such as PDMSs, optionally phenylated, such as phenyltrimethicones.

The oily phase may also comprise a makeup-removing oil such as a fatty acid ester, in particular the esters obtained from a straight- or branched-chain alcohol having from 1 to 17 carbon atoms and from a straight- or branched-chain fatty acid having from 3 to 18 carbon atoms.

Representative such esters include dioctyl adipate, 2-ethylhexyl palmitate, diisopropyl adipate, 2-ethylhexyl hexanoate, ethyl laurate, methyl myristate, octyldodecyl octanoate, isodecyl neopentanoate, ethyl myristate, myristyl propionate, 2-ethylhexyl 2-ethylhexanoate, 2-ethylhexyl octanoate, 2-ethylhexyl caprate/caprylate, methyl palmitate, butyl myristate, isobutyl myristate, ethyl palmitate, isohexyl laurate, hexyl laurate and isopropyl isostearate.

The oily phase advantageously constitutes from 5%–95% by weight in the case of an emulsion.

The compositions according to the invention may also comprise, in addition:

(i) an agent permitting the fatty phase to be placed in suspension, for example a copolymer of $C_{10}$–$C_{30}$ alkyl acrylates and of acrylic or methacrylic acid or ester thereof(Pemulen TR1, Pemulen TR2 and Carbopol 1342 marketed by Goodrich); or an acrylamide/methylpropanesulfonic acid copolymer (Sepigel marketed by SEPPIC), and/or (ii) an agent for dispersing the fatty phase, such as an emulsifying or vesicular system based on vesicles, optionally of nanometric size, comprising ionic lipids (liposomes) or nonionic lipids, and in particular the emulsifying systems which are well known to the art, and comprising glyceryl stearate/PEG 100 stearate (CTFA), cetyl alcohol and stearyl alcohol.

The compositions of the invention too may comprise an agent for modifying its viscosity, and for providing more or less gelled textures, such as:

(iii) cellulose derivatives (carboxymethylcellulose, hydroxyethylcellulose or hydroxypropylmethylcellulose), (iv) natural gums such as xanthan gum, guar gum or carob gum, scleroglucans, chitin or chitosan derivatives, and carrageenans, (v) polycarboxyvinyl derivatives such as Carbomer (marketed by Goodrich under the trademarks Carbopol 940, 951 and 980, or by 3V-Sigma under the trademark Synthalen K or Synthalen L).

The compositions according to the invention may also comprise conventional additives and adjuvants for cosmetic/dermatological applications, such as preservatives, antioxidants, fragrances, fillers such as kaolin or starch, or even hollow microspheres, pigments, UV screening agents, sequestering agents, essential oils, dyestuffs, colorants, odor absorbers, hydrophilic or lipophilic active agents such as moisturizers, in particular glycerol or butylene glycol, anti-inflammatory agents such as allantoin and bisabolol, anti-free-radical agents such as alantoin or bisabolol, anti-free-radical agents such as vitamin E or derivative thereof, soothing agents such as cornflower water or extract of iris, depigmenting agents, biological active agents such as urea, amino acids, vitamins and derivative thereof, proteins, salicylic acid and derivatives thereof, α-hydroxy acids, pyrrolidonecarboxylic acid and its salts, and ceramides.

One skilled in this art will of course take care to select this or these optional complementary compounds, and/or the amount thereof, such that the advantageous properties of the compositions according to the invention are not, or are not substantially, adversely affected by the addition envisaged.

The subject compositions preferably have a pH which does not damage the skin, generally ranging from 5 to 8, preferably a pH of from 5.5 to 7.5.

The compositions of the invention are well suited for cosmetic or pharmaceutical use, particularly dermatological use.

The subject compositions are typically formulated for topical application/administration.

In order to further illustrate the present invention and the advantages thereof, the following specific examples are given, it being understood that same are intended only as illustrative and in nowise limitative.

EXAMPLE 1

The capacity of Cinnamic Acid to Promote Desquamation of the Skin was Examined

This test of in vitro screening of an active agent on desquamation was carried out on differentiated human keratinocytes. The principle of the test was based on the fact that desquamation induces the release of corneocytes. The desquamating power of the product tested will be proportionately greater the larger the number of corneocytes released.

The test procedure was as follows: starting with human skin biopsies, the keratinocytes obtained by separation of the epidermis were dissociated by enzymatic action with trypsin and were cultured at a concentration of $2\times10^5$ cells/ml. Growth and differentiation of the keratinocytes were obtained by culturing for 10 to 20 days in a specific medium. Next, after removing the culture medium, the activity of the test product was evaluated. To do this, two samples were taken at T0 and T60, i.e., just before adding the product and 60 minutes after this addition. The samples thus taken were analyzed with a flow cytometer in order to count the corneocyte population. The flow cytometer made it possible to distinguish the corneocyte and keratinocyte populations by treatment with acridine orange, which is specific for cellular DNA. This staining was specific for the keratinocytes since normal corneocytes do not contain a nucleus and thus no DNA.

The cellular detachment index was determined by the difference between T60 and T0. The same measurement was carried out for a control containing no test product, since the experimental conditions inevitably induced the release of corneocytes, even in the absence of active agents.

The test was carried out with cinnamic acid at a concentration of $5\times10^{-5}$M.

The results of these studies are reported in the Table below:

TABLE

| Compounds at $5 \times 10^{-5}$M | % | p** |
|---|---|---|
| Reference* | 96.6 | <0.05 |
| Cinnamic acid | 59.2 | >0.05 |
| Control | 0 | — |

*Reference: 2-hydroxy-5-octanoylbenzoic acid, which is known to promote desquamation (FR-85/06953 assigned to the assignee hereof).
**:p: confidence interval calculated according to the Dunett method.

The results are given as a % of activity relative to the control consisting of an identical culture in the absence of compound.

The activity of the cinnamic acid on the cellular detachment, thus, was high.

EXAMPLE 2

Examples of Specific Formulations According to the Invention: These Compositions were Forulated by Simple Intimate Admixing of the Various Components Composition 1: Facial Milk

| | |
|---|---|
| Liquid petroleum jelly | 7.0 g |
| Cinnamic acid | 2.0 g |
| Glyceryl monostearate, polyethylene glycol stearate (100 EO) | 3.0 g |
| Carboxyvinyl polymer | 0.4 g |
| Stearyl alcohol | 0.7 g |
| Soybean proteins | 3.0 g |
| NaOH | 0.4 g |
| Preservative | qs |
| Water | qs 100 g |

This composition was in the form of a facial milk having good cosmetic properties and was mild and comfortable to use.

The pH of the composition was about 5.5.

Composition 2: Lotion

| | |
|---|---|
| Cinnamic acid | 0.5 g |
| 2-Ethylhexyl palmitate | 10.0 g |
| Cyclopentadimethylsiloxane | 20.0 g |
| Butylene glycol | 5.0 g |
| Preservative | qs |
| Water | qs 100 g |

This lotion, which contained no surfactant, promoted desquamation of the skin.

Composition 3: Milk

| | |
|---|---|
| Octyl palmitate | 35.0 g |
| Glycerol | 2.0 g |
| Cinnamic acid | 2.0 g |
| C10–C30 acrylates/alkylacrylates crosslinked polymer | 0.1 g |
| Triethanolamine | 0.1 g |
| Amino acids from wheat | 1.0 g |

-continued

|                            |           |
| -------------------------- | --------- |
| Preservative               | qs        |
| Water                      | qs 100 g  |

The milk obtained, which contained no surfactant, had good cosmetic properties.

Composition 4: Facial Gel

|                            |          |
| -------------------------- | -------- |
| Glycerol                   | 10.0 g   |
| Cinnamic acid              | 1.0 g    |
| Disodium cocoamphodiacetate| 1.0 g    |
| Preservative               | qs       |
| Water                      | qs 100 g |

The gel obtained had good cosmetic properties.

Composition 5: Cleansing Gel with Water

|                            |          |
| -------------------------- | -------- |
| Butylene glycol            | 7.0 g    |
| Sodium lauroyl sarcosinate | 4.0 g    |
| Cinnamic acid              | 0.5 g    |
| Triethanolamine            | 0.8 g    |
| Carbomer                   | 0.5 g    |
| Preservatives              | qs       |
| Water                      | qs 100 g |

The gel obtained had good cosmetic properties.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for promoting desquamation or stimulating epidermal renewal of the skin of a human subject in need of such treatment, comprising topically applying thereto a cosmetic or dermatological composition comprising a desquamation-effective or epidermal renewal-effective amount of cinnamic acid or at least one derivative of cinnamic acid which is selected from the group consisting of mono- and polyhydroxy cinnamic acids, alcohols and aldehydes thereof, formulated into a topically applicable, cosmetically or dermatologically acceptable vehicle, diluent or carrier therefor.

2. A method for promoting desquamation of the skin of a human subject in need of such treatment, comprising topically applying thereto a cosmetic or dermatological composition comprising a desquamation-effective amount of cinnamic acid or at least one derivative of cinnamic acid which is selected from the group consisting of mono- and polyhydroxy cinnamic acids, alcohols and aldehydes thereof, formulated into a topically applicable, cosmetically or dermatologically acceptable vehicle, diluent or carrier therefor.

3. A method for stimulating renewal of the epidermal skin of a human subject in need of such treatment, comprising topically applying thereto a cosmetic or dermatological composition comprising an epidermal renewal-effective amount of cinnamic acid or at least one derivative of cinnamic acid which is selected from the group consisting of mono- and polyhydroxy cinnamic acids, alcohols and aldehydes thereof, formulated into a topically applicable, cosmetically or dermatologically acceptable vehicle, diluent or carrier therefor.

4. The method as defined by claim 1, wherein said composition includes only ingredients or amounts thereof which do not cause the side-effect sensations of stinging, tautness, overheating or redness of the skin.

5. The method as defined by claim 1, wherein a desquamation-effective or epidermal renewal-effective amount of cinnamic acid is topically applied to said skin.

6. The method as defined by claim 1, wherein the amount of cinnamic acid or derivative thereof present in the composition ranges from $10^{-6}\%$ to 10% by weight of the total weight.

7. The method as defined by claim 6, wherein the amount of cinnamic acid or derivative thereof present in the composition ranges from $10^{-3}\%$ to 5% by weight of the total weight.

8. The method as defined by claim 1, wherein said composition has a pH ranging from 5 to 8.

9. The method as defined by claim 2, wherein a desquamation-effective amount of cinnamic acid is topically applied to said skin.

10. The method as defined by claim 3, wherein an epidermal renewal-effective amount of cinnamic acid is topically applied to said skin.

11. The method as defined by claim 5, wherein the amount of cinnamic acid present in the composition ranges from 0.5% to 2% by weight of the total weight.

12. The method as defined by claim 9, wherein the amount of cinnamic acid present in the composition ranges from 0.5% to 2% by weight of the total weight.

13. The method as defined by claim 10, wherein the amount of cinnamic acid present in the composition ranges from 0.5% to 2% by weight of the total weight.

* * * * *